United States Patent
Chang (10) Patent No.: US 11,911,598 B2
(45) Date of Patent: Feb. 27, 2024

(54) DEVICE FOR INJECTING FIXED QUANTITY OF LIQUID MEDICINE

(71) Applicant: JMBIOTECH CO., LTD., Daegu (KR)

(72) Inventor: Ji-young Chang, Daegu (KR)

(73) Assignee: JMBIOTECH CO., LTD., Daegu (KR)

( * ) Notice: Subject to any disclaimer, the term of this patent is extended or adjusted under 35 U.S.C. 154(b) by 233 days.

(21) Appl. No.: 17/405,779

(22) Filed: Aug. 18, 2021

(65) Prior Publication Data

US 2023/0056435 A1    Feb. 23, 2023

(51) Int. Cl.
*A61M 5/315*        (2006.01)
*A61M 5/20*         (2006.01)

(52) U.S. Cl.
CPC ...... *A61M 5/31526* (2013.01); *A61M 5/2033* (2013.01); *A61M 5/31501* (2013.01); *A61M 5/31511* (2013.01); *A61M 2005/31508* (2013.01)

(58) Field of Classification Search
CPC .......................... A61M 5/3295; A61M 5/315; A61M 5/31511; A61M 5/31501; A61M 5/2033; A61M 5/31526; A61M 2005/3152; A61M 2005/31508; A61M 2005/5033; A61M 5/31576; A61M 5/31578
USPC ......................................................... 604/135
See application file for complete search history.

(56) References Cited

U.S. PATENT DOCUMENTS

2010/0030152 A1*   2/2010   Lee ................... A61M 37/0015
                                                                      604/131
2010/0175779 A1    7/2010   Ogawa et al.
2012/0136306 A1*   5/2012   Bartha .................... A61M 5/30
                                                                      604/154
2019/0175839 A1    6/2019   Kwolek et al.
2020/0188610 A1    6/2020   Fretta et al.

FOREIGN PATENT DOCUMENTS

| CA | 2356936 A1 | 7/2000 |
|---|---|---|
| EP | 0651662 B1 | 9/1999 |
| JP | 2006-502768 A | 1/2006 |
| JP | 2009-268660 A | 11/2009 |
| JP | 2020-188858 A | 11/2020 |
| KR | 10-2004-0030900 A | 4/2004 |
| KR | 10-2009-0064525 A | 6/2009 |
| KR | 10-2011-0098398 A | 9/2011 |
| KR | 101939061 B1 | 1/2019 |

OTHER PUBLICATIONS

European Search Report dated Dec. 7, 2021 for European Patent Application No. 21191828.9.

* cited by examiner

*Primary Examiner* — Theodore J Stigell
*Assistant Examiner* — Nidah Hussain

(57) ABSTRACT

Provided is a device for injecting a fixed quantity of liquid medicine, to which a syringe may be mounted and which may inject the liquid medicine held in the syringe by a fixed quantity due to a user's pushing operation. The device for injecting the fixed quantity of liquid medicine is advantageous in that a user can operate the device with one hand to inject the fixed quantity of medicine into various areas, thus maximizing operability and convenience. Furthermore, the device is advantageous in that it is possible to maximize medicine delivery efficiency even when operated by a person who is not a medical staff not in a hospital but at home.

12 Claims, 13 Drawing Sheets

DEVICE FOR INJECTING FIXED QUANTITY OF LIQUID MEDICINE

BACKGROUND OF THE DISCLOSURE

Field of the Disclosure

The present disclosure relates to a device for injecting a fixed quantity of purposed liquid solution such as medicine, cosmetic and, more particularly, to a device for injecting a fixed quantity of liquid medicine, which is capable of delivering medicine to a large area of target tissue by a user's operation.

Related Art

A method of applying medicine to a skin surface so as to deliver medicine to specific tissue in a thin form, such as skin, is widely used. However, the method of applying the medicine to the skin surface is problematic in that an absorption rate is low, so it is difficult to obtain appropriate therapy effect. In order to solve the problem, recently, a method in which a needle of a short length is used to penetrate into the skin tissue and thereby deliver medicine is developed and used. Such a related art is disclosed in Korean Patent No. 1939061.

However, the related art is problematic in that this does not satisfy a case where extreme convenience is required, such as when self-injection is performed, for example, a user injects medicine into his or her face.

SUMMARY OF THE DISCLOSURE

The present disclosure provides a device for injecting a fixed quantity of liquid medicine, which is capable of delivering a fixed quantity of medicine to skin through a simple operation by maximizing convenience.

In an aspect, a device for injecting a fixed quantity of liquid medicine may include an upper housing through which a first cavity is vertically formed, a lower housing configured to be connectable to a lower portion of the upper housing, with a second cavity being vertically formed through the lower housing, a cap disposed in an upper portion of the first cavity, and configured such that at least a portion thereof linearly reciprocates in the first cavity, and a fixed-quantity moving module moved downwards by a preset distance for each vertical reciprocating movement of the cap to push a piston of the syringe.

The fixed-quantity moving module may include a first pushing block configured to receive a force from a lower end of the cap and thereby move downwards, with a hollow portion being vertically formed in the first pushing block, and a pushing bar extending to a predetermined length to be inserted into the upper housing and the hollow portion of the first pushing block, and supported at a first side thereof to move downwards by a predetermined distance as the first pushing block moves downwards.

A lower portion of the pushing bar may be configured such that at least a portion thereof is inserted into the syringe.

A lower end of the pushing bar may be inserted into the syringe to press the piston of the syringe.

The pushing bar may include a linear ratchet gear which is longitudinally formed on a side surface of the pushing bar, the first pushing block may include a first pawl engaging with the ratchet gear, and the linear ratchet gear and the first pawl may be configured to move the pushing bar downwards and limit an upward movement thereof.

The device may further include a second pushing block provided in the first cavity under the first pushing block to be spaced apart therefrom by a predetermined distance, and the second pushing block may include a hollow portion formed to allow the pushing bar to be vertically inserted therein, and a second pawl engaging with the linear ratchet gear to move the pushing bar downwards.

The device may further include a first spring provided between the cap and the first pushing block, and a second spring provided between the first pushing block and the second pushing block.

The device may further include a guide ring having a hollow portion formed in a vertical direction to allow the pushing bar to be inserted therein, and configured such that a first side thereof supports a bottom of the second pushing block and a second side thereof is fixed in the first cavity.

The first pushing block may be configured to move to a position where the first pushing block is in close contact with the second pushing block when the first pushing block is pressed downwards by the cap, and be configured to return to an original position thereof by the second spring when the first pushing block is not pressed.

When a downward force is transmitted to the first pushing block by the cap, the first pushing block may move downwards along with the pushing bar while limiting a relative movement of the linear ratchet gear by the first pawl, and the second pawl of the second pushing block may permit the relative movement of the linear ratchet gear in a state where a position of the second pawl is fixed.

When the downward force is removed from the first pushing block, the first pushing block may be moved upwards by the second spring, the relative movement of the linear ratchet gear may be limited by the second pawl of the second pushing block, and the first pawl of the first pushing block may permit the relative movement of the linear ratchet gear.

The pushing bar may include a plurality of linear ratchet gears, and a number of each of the first and second pawls may correspond to a number of the linear ratchet gears.

The device may further include a tip configured to be connected to a needle adapter of the syringe in a state where the syringe is inserted into the second cavity.

The tip may include a plurality of needles and an internal path configured to fluidly communicate with the needle adapter, the needles each may be configured to fluidly communicate with the internal path, and be arranged to be spaced apart from each other, a portion of a lower end of each of the needles protruding downwards from a lower surface of the tip.

A device for injecting a fixed quantity of liquid medicine according to the present disclosure is advantageous in that a user can click and operate the device with one hand to pump and inject a fixed quantity of purposed liquid solution such as medicine to various areas, thus maximizing operability and convenience.

Furthermore, the device is advantageous in that it is possible to maximize medicine delivery efficiency even when operated by a person who is not a medical staff not in a hospital but at home.

DESCRIPTION OF EXEMPLARY EMBODIMENTS

Hereinafter, a device for injecting a fixed quantity of liquid medicine according to an embodiment of the present disclosure will be described with reference to the accompanying drawings. Further, in the description of the following embodiment, the term of each component may be referred to as another term used in the art. However, even if a modified embodiment is employed, it can be regarded as an equivalent configuration as long as its function remains similar or identical. Further, reference numerals added to respective components are used for the convenience of description. However, contents denoted by the reference numerals in the drawings do not limit the respective components to the scope of these drawings. Likewise, even if an embodiment in which components of the drawings are partially modified is employed, it can be regarded as an equivalent configuration as long as its function remains similar or identical. Further, if those skilled in the art recognize that a component is essential herein, a description thereof will be omitted.

Meanwhile, hereinafter, an orientation of a device for injecting a fixed quantity of liquid medicine shown in FIG. 1 will be defined as a vertical direction. In other words, it will be described on the premise that a portion where a cap to be described later is disposed is an upper portion, and a portion where a tip to be described later is disposed is a lower portion.

Hereinafter, the configuration of the device 1 for injecting the fixed quantity of liquid medicine according to an embodiment of the present disclosure will be described in detail with reference to FIGS. 1 to 4.

Figure 1:
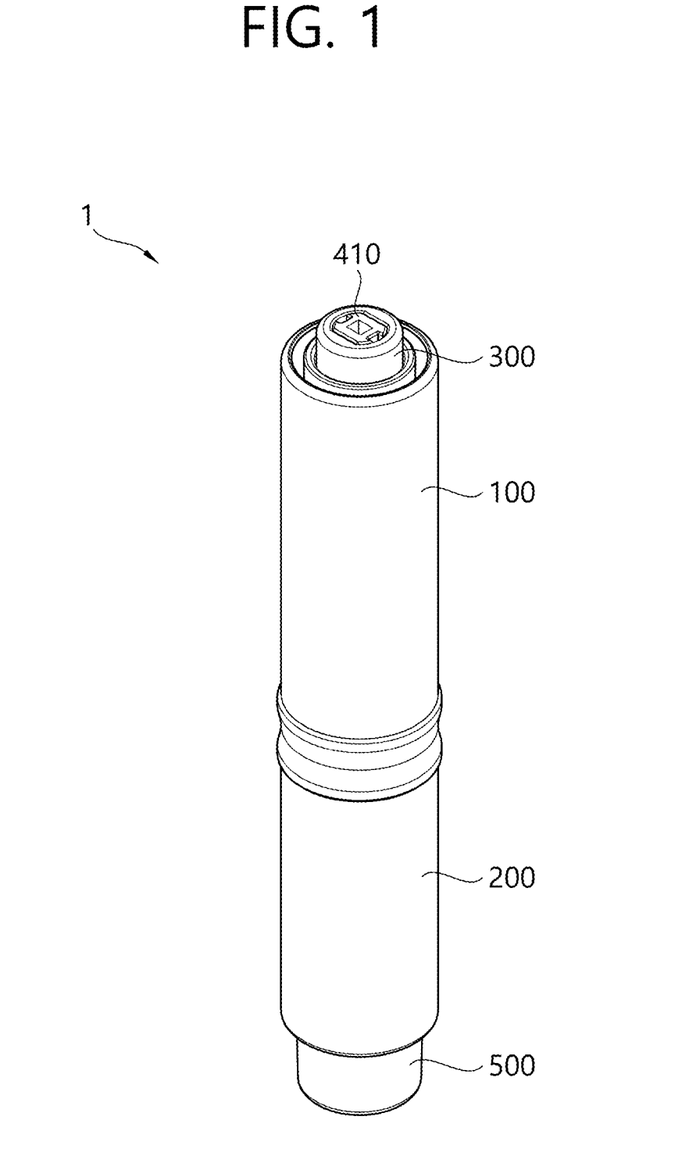
FIG. 1 is a front view showing a device for injecting a fixed quantity of liquid medicine according to an embodiment of the present disclosure.
Figure 2:
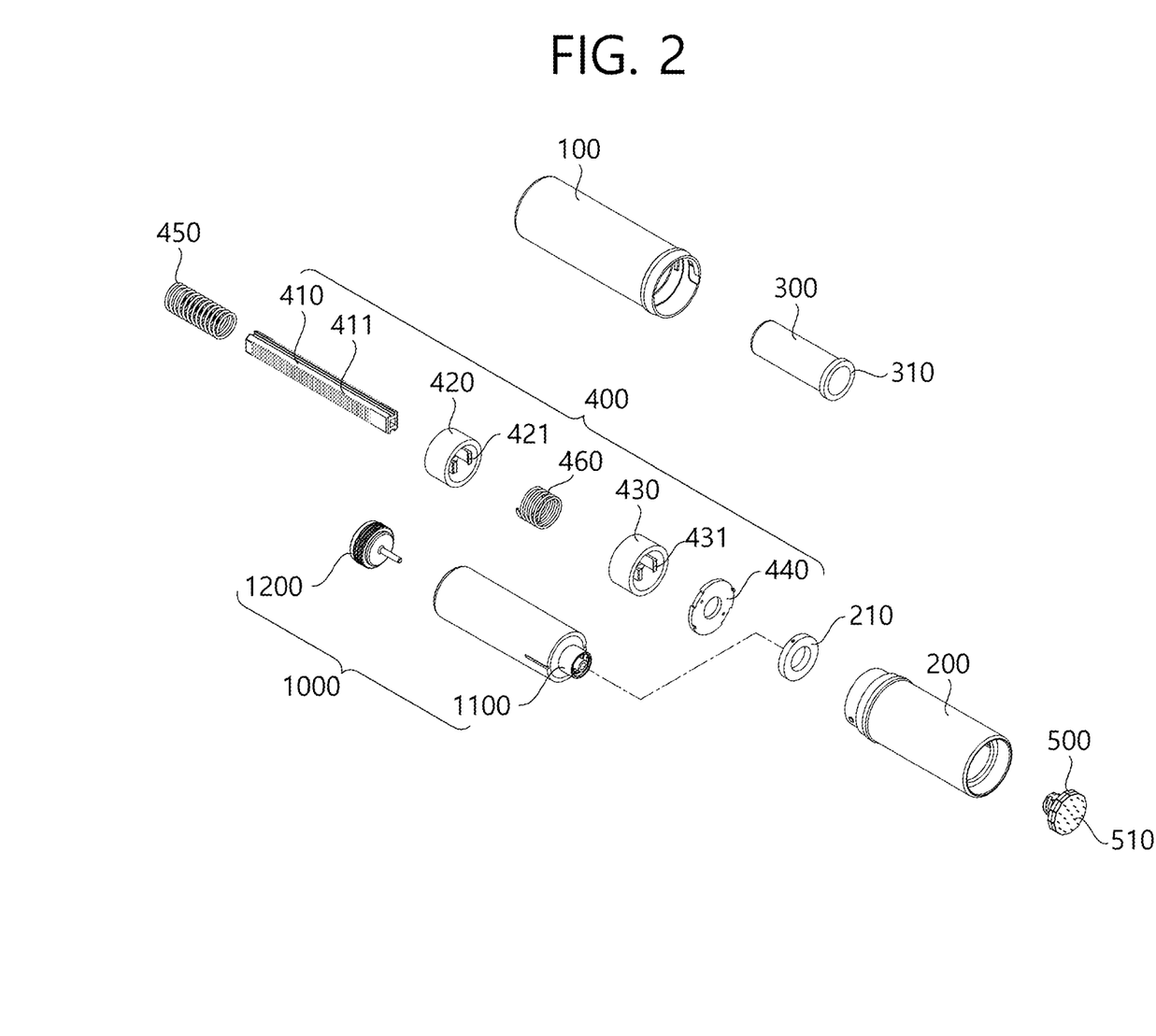
FIG. 2 is an exploded perspective view showing the device for injecting the fixed quantity of liquid medicine according to the embodiment of the present disclosure.
Figure 3:
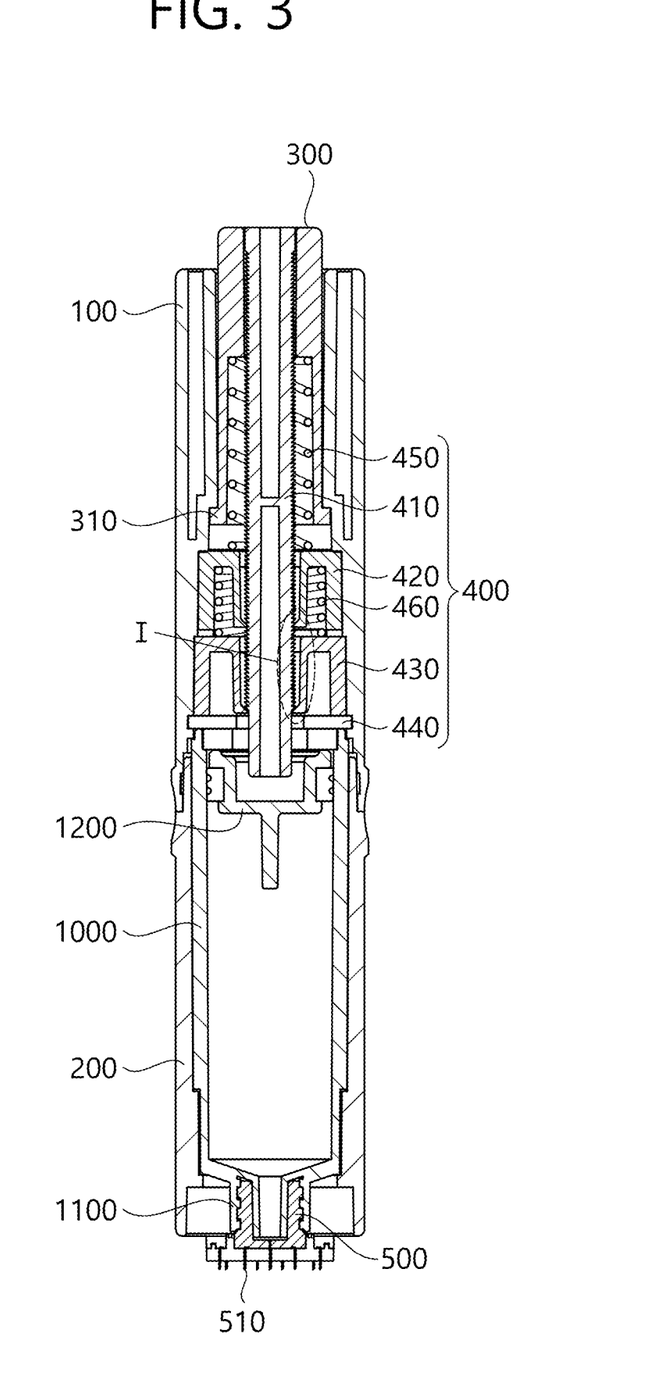
FIG. 3 is a sectional view showing the device for injecting the fixed quantity of liquid medicine according to the embodiment of the present disclosure.
Figure 4:
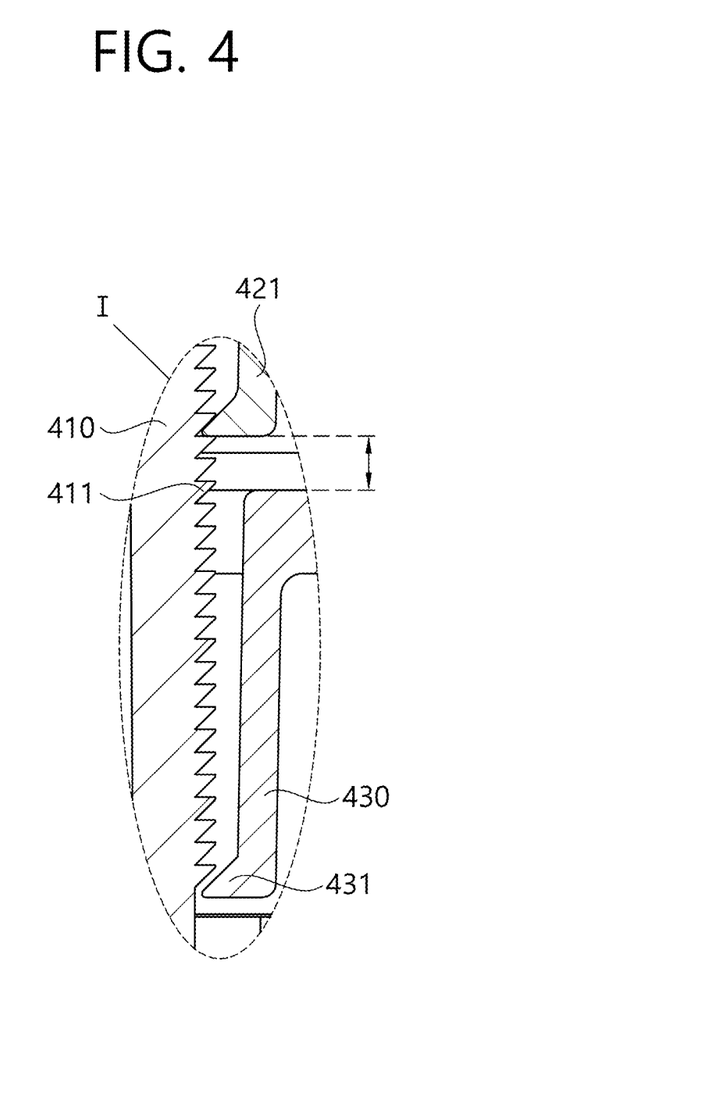
FIG. 4 is an enlarged sectional view showing portion I of FIG. 3.

FIG. 1 is a front view showing a device 1 for injecting a fixed quantity of liquid medicine according to an embodiment of the present disclosure, FIG. 2 is an exploded perspective view showing the device 1 for injecting the fixed quantity of liquid medicine according to the embodiment of the present disclosure, FIG. 3 is a sectional view showing the device 1 for injecting the fixed quantity of liquid medicine according to the embodiment of the present disclosure, and FIG. 4 is an enlarged sectional view showing portion I of FIG. 3.

Referring to FIGS. 1 to 4, the device 1 for injecting the fixed quantity of liquid medicine according to the embodiment of the present disclosure may be configured to press a syringe 1000 accommodated therein while a fixed quantity is moved as the device performs a reciprocating operation once by a user. In other words, a piston 1200 of the syringe 1000 may be moved by a fixed distance by a single operation. As the piston 1200 is moved in the syringe 1000, a fixed quantity of liquid medicine may be discharged through a needle 510 of a tip 500. That is, the device may be formed of a pen type, and may be formed of a click type pump system which injects liquid medicine or cosmetic by clicking.

The device may include an upper housing 100, a lower housing 200, a cap 300, a syringe 1000, a fixed-quantity moving module 400, and the tip 500.

Each of the upper housing 100 and the lower housing 200 may have a hollow portion which is vertically formed therein, and the syringe 1000 and the fixed-quantity moving module 400 may be provided in the hollow portion.

The upper housing 100 and the lower housing 200 may be vertically assembled with each other to be used, and may be disassembled from each other to insert and remove the syringe 1000 and to reset the position of a pushing bar 410 which will be described below. Each of the upper housing 100 and the lower housing 200 may be formed in a cylindrical shape to enhance convenience when a user grips and operates the device.

The upper housing 100 may extend vertically to a predetermined length, and may be configured such that a first cavity 101 is vertically formed therein and the fixed-quantity moving module 400 and the cap 300 are provided therein. A guide ring 440 may be provided on a lower portion of the upper housing 100 to prevent a second pushing block 430 of the fixed-quantity moving module 400 from being removed downwards. The guide ring 440 may prevent the second pushing block 430 which will be described below from being moved downwards, and may have a hollow portion in a central portion thereof to allow the pushing bar 410 to pass therethrough.

A cap support portion 110 may be provided in an upper portion of the upper housing 100 to prevent the removal of the cap 300. The cap support portion 110 may be formed in the first cavity 101 to protrude towards a central axis by a predetermined length. The cap support portion 110 may be configured such that a side of the cap 300 passes therethrough but a cap protrusion 310 which will be described below does not pass therethrough. Thus, the upward movement of the cap 300 beyond a predetermined distance is limited by the cap support portion 110.

The lower housing 200 may vertically extend to a predetermined length, and may be fastened to a lower portion of the upper housing 100. A second cavity 201 may be vertically formed in the lower housing 200. The syringe 1000 may be inserted into the second cavity 201 in a direction from a top to a bottom of the lower housing 200.

A syringe support portion 210 may be provided on a lower portion of the lower housing 200 to radially protrude towards the second cavity 201. The syringe support portion 210 supports a bottom of the syringe 1000 when the syringe 1000 is inserted into the second cavity 201. Further, a hole may be formed in a central portion of the syringe support portion 210, and a needle adapter 1100 of the syringe 1000 is inserted into the hole.

The cap 300 may be provided on the upper portion of the upper housing 100, and at least a portion of the cap may be inserted into the first cavity 101. The cap 300 may be moved vertically by a user's pushing operation and may be configured such that an upward removal thereof is limited. The cap 300 may be inserted into the upper portion of the second cavity 201, and the cap protrusion 310 may be provided on the lower portion of the cap 300 and protrude radially to engage with the cap support portion 110. A hollow portion is formed in the central portion of the cap 300 to allow a pushing bar 410, which will be described below, to be vertically inserted therein. This will be described later in detail with reference to FIG. 8.

The fixed-quantity moving module 400 is configured such that an end thereof may move downwards to a predetermined distance, if a user presses the cap 300. The fixed-quantity moving module 400 is configured such that at least a portion thereof may be disposed in the first cavity 101 and at least a portion thereof may be in close contact with the piston 1200 in the syringe 1000 mounted on the second cavity 201.

The fixed-quantity moving module 400 may include a pushing bar 410, a first pushing block 420, a second pushing block 430, a first spring 450, and a second spring 460. The pushing bar 410 may extend longitudinally, and may be configured to be moved downwards by the support operation of the first pushing block 420 and the second pushing block 430.

The pushing bar 410 may have an outer diameter to be inserted into the cap 300, the second cavity 201, and the syringe 1000. At least one linear ratchet gear 411 may be provided on a side surface of the pushing bar 410. By way of example, ratchet gears 411 may be provided on opposite side surfaces of the pushing bar 410. The gear-tooth inclination of the ratchet gear 411 may be determined such that the pushing bar may be moved only downwards by the first pushing block 420 and the second pushing block 430. For example, the upper surface of each gear tooth of the ratchet gear 411 may be horizontally formed, and at least a portion of the lower surface thereof may be formed as a surface inclined downwards as it becomes distant from the center of the pushing bar 410.

The first pushing block 420 and the second pushing block 430 are vertically arranged, and may be configured to move the pushing bar 410 downwards to a predetermined distance as a distance between the first and second pushing blocks is adjusted. The first pushing block 420 may include a first pawl 421 engaging with the ratchet gear 411. The first pawl 421 may extend from a top to a bottom of the first pushing block 420, and may have on a lower end gear teeth facing the central axis extending in the vertical direction. The lower surface of each gear tooth of the first pawl 421 may be horizontally formed, and at least a portion of the upper surface of the tooth may be formed as a surface inclined downwards as it goes towards the central axis.

Similarly to the first pushing block 420, the second pushing block 430 may be provided with a second pawl 431. The second pawl 431 may extend to a predetermined length in a direction from a top to a bottom of the second pushing block 420, and may have gear teeth. The direction of each gear tooth may also be the same as that of the first pawl 421.

Since each of the first pawl 421 and the second pawl 431 is formed of an elastic material, it may be bent when the ratchet gear 411 is moved downwards. Thus, when the teeth of the ratchet gear 411 pass through the gear teeth of the first and second pawls 421 and 431 and return to their original positions, the first and second pawls may be configured to support the upper surface of each tooth of the ratchet gear 41.

The first spring 450 may be provided between the cap 300 and the first pushing block 420, and may provide an upward force to restore the cap 300, which has moved downwards, to an original position thereof.

The second spring 460 may be provided between the first pushing block 420 and the second pushing block 430, and may provide an upward force to restore the first pushing block 420, which has moved downwards, to an original position thereof.

Meanwhile, each of the above-described first pushing block 420, second pushing block 430, first spring 450, and second spring 460 may have a space into which the pushing bar 410 may be inserted.

The tip 500 may be provided on the lower portion of the lower housing 200, and may be detachably provided on the syringe support portion 210. An upper portion of the tip 500 may be connected to the syringe support portion 210, and may fluidly communicate with the needle adapter 1100 of the syringe 1000. A plurality of needles 510 may be provided on an end of the tip 500 to protrude from an end surface thereof to a predetermined length. An internal path may be provided in the tip 500 to allow the needle adapter 1100 of the syringe 1000 and each of the needles 510 to fluidly communicate with each other. Thus, the liquid medicine leaked to an outside by pressing the syringe 1000 may be discharged through the plurality of needles 510. Meanwhile, the outer surface of the upper end of the tip may be in close contact with the lower portion of the syringe support portion 210 to be fixed, and the inner surface thereof may be configured to allow the needle adapter 1100 to be inserted therein.

Here, the needle equipped with the needle adapter 1100 having various outer diameters depending on the inner diameter of the upper end of the tip may be used, and the needle equipped with a needle adapter having a smaller outer diameter may be used without changing its structure. Meanwhile, a connecting structure between the upper end of the tip and the syringe support portion 210 may be changed in various ways.

The protruding length of the needles 510 may be determined to allow the needles 510 to be inserted into the skin when the bottom surface of the tip 500 is in close contact with the surface of the skin. Preferably, the protruding length of the needles 510 may be within 2 mm.

The tip may be provided with various types of needles. The tip can perform the function of injecting medicine solution and stimulating the skin depending on the type of needle. Specifically, the needle of the tip can reach the skin surface, superficial layer, epidermis layer, and targeting skin layer depending on the type of needle to stimulate tissue and/or purposed liquid solution such as medicine can be injected.

Turning back to FIGS. 3 and 4, the cap 300 and the first pushing block 420, and the first pushing block 420 and the second pushing block 430 may be vertically provided to be spaced apart from each other by a predetermined distance.

Particularly, a vertical separation distance between the first pushing block 420 and the second pushing block 430 may be determined as a distance to be moved when a user performs one pushing operation. By way of example, the first and second pushing blocks may be spaced apart from each other by the length of two ratchet gears 411. Meanwhile, the number of each of the first and second pawls 421 and 431 may correspond to the number of the ratchet gears 411 provided on the pushing bar 410.

Hereinafter, the operation of the fixed-quantity moving module 400 will be described in detail with reference to FIGS. 5A, 5B, and 5C.

Figure 5A:
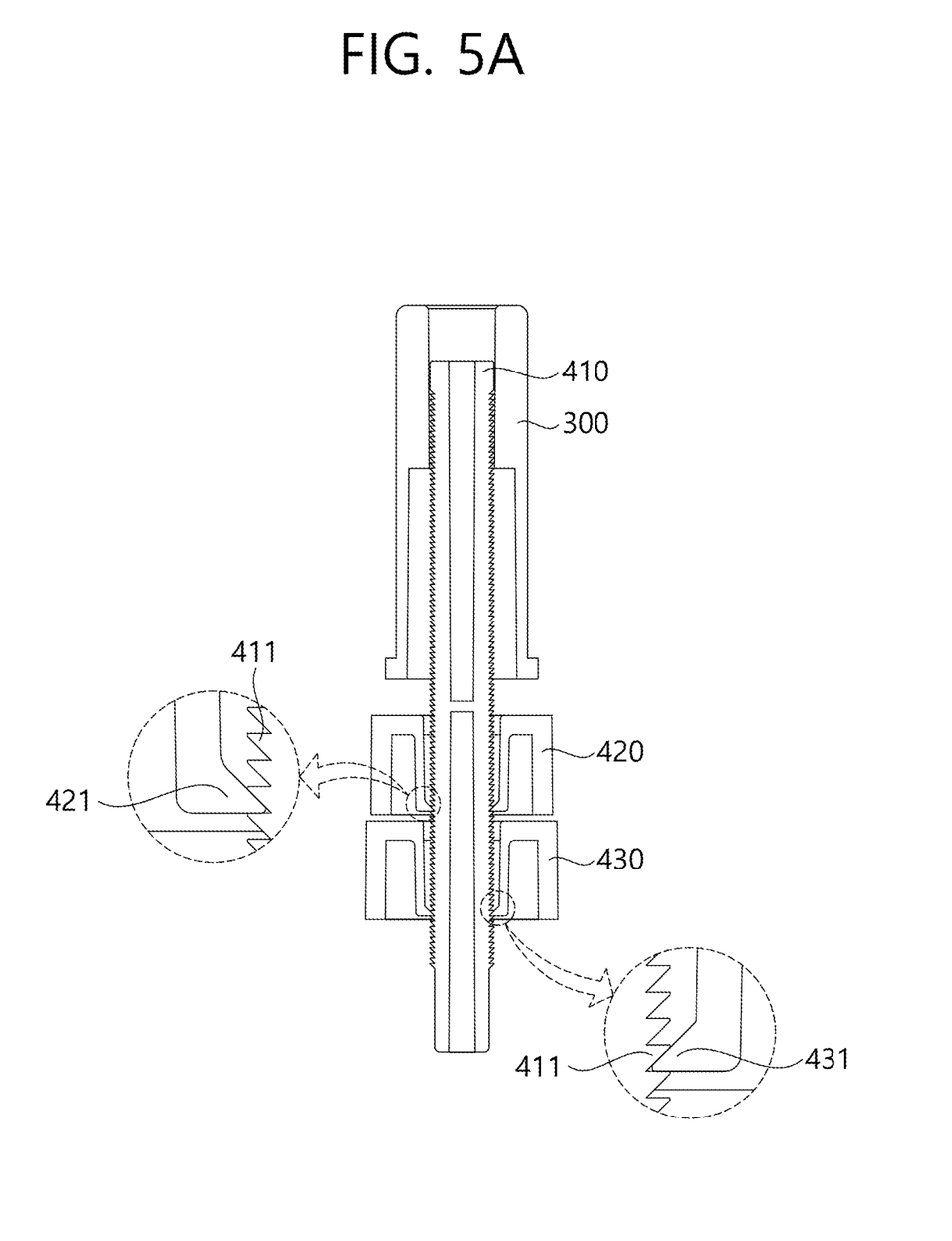
FIGS. 5A, 5B, and 5C are diagrams showing the operation of a pushing block by a user's operation.
Figure 5B:
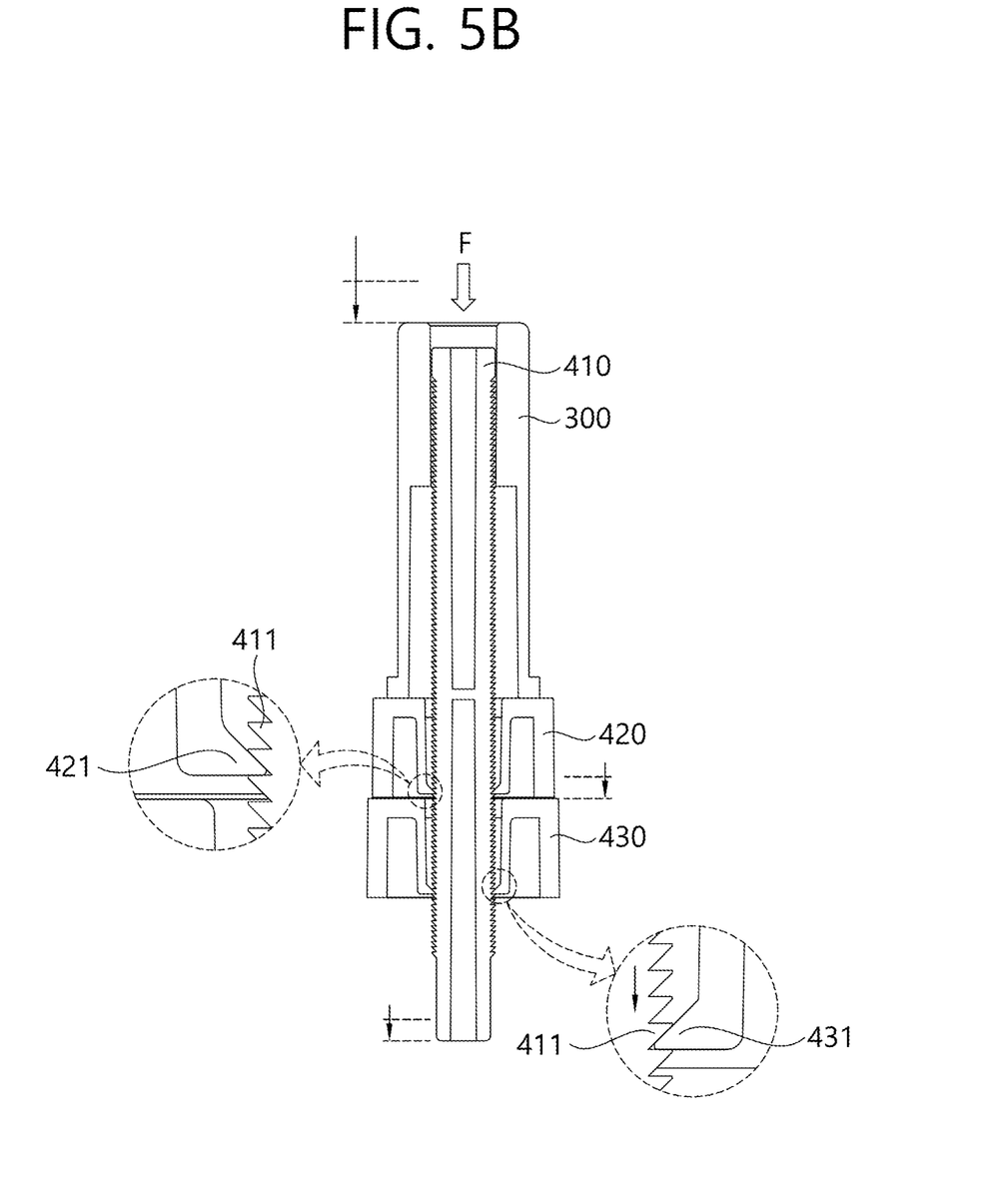
Figure 5C:
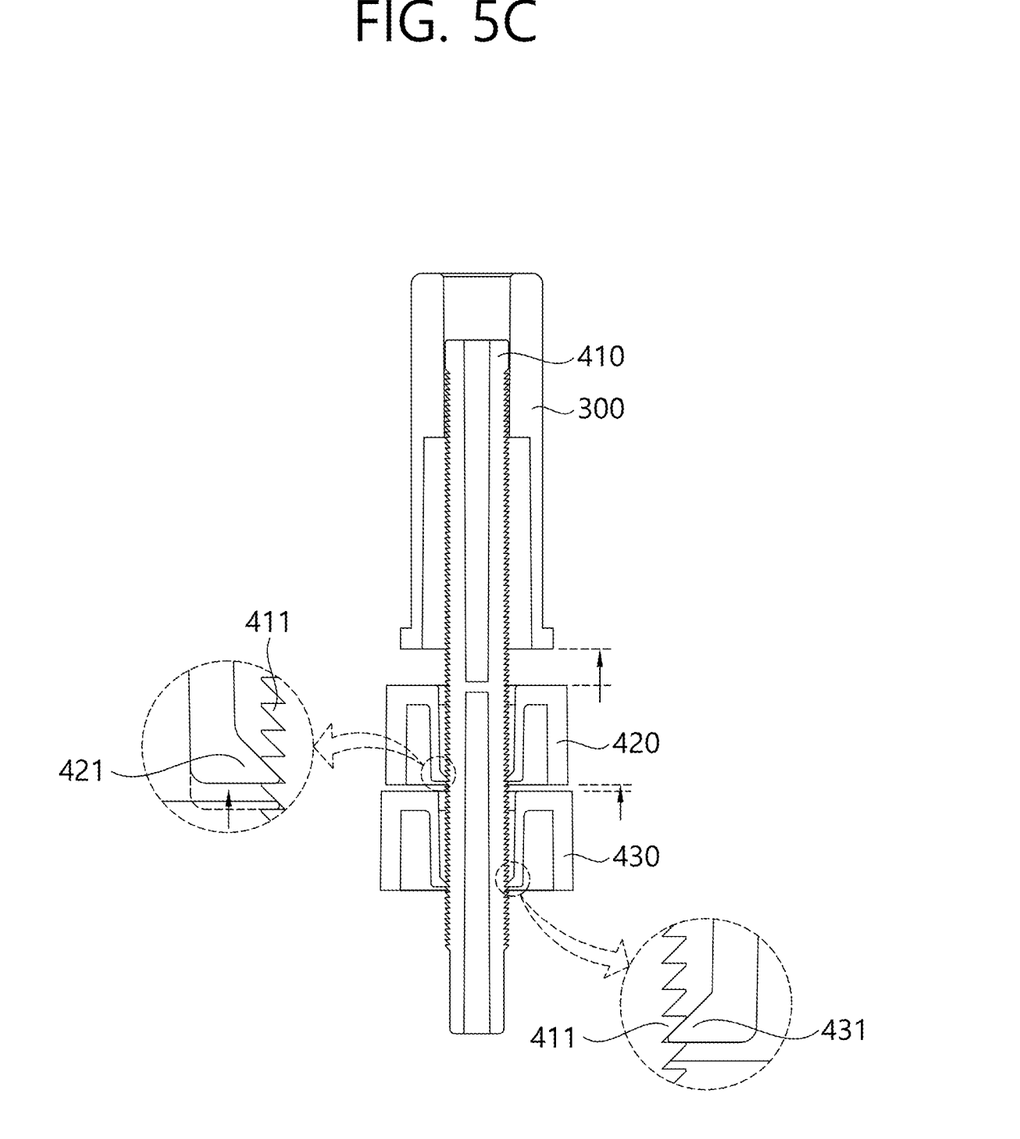

FIGS. 5A, 5B, and 5C are diagrams showing the operation of the pushing block by a user's operation.

First, referring to FIG. 5A, as described above with reference to FIG. 4, the cap 300 may be provided on the upper portion of the first pushing block 420, and may be supported by the first spring 450 to be disposed on the uppermost portion of the first cavity 101. A lower portion of the second pushing block 430 may be supported by the guide ring 440 to limit a downward movement. The first pushing block 420 may be provided between the cap 300 and the second pushing block 430. An upper portion of the first pushing block may be supported by the first spring 450, while a lower portion thereof may be supported by the second spring 460.

In a standby state, the first pushing block 420 and the second pushing block 430 may be disposed to be spaced apart from each other by the second spring 460. In this regard, as described above, the separation distance may be determined as the length of a pushing bar which is to be moved downwards when a user performs a pushing operation once.

Subsequently, referring to FIG. 5B, when a user presses the cap 300 downwards, the cap 300 moves down and comes into close contact with the first pushing block 420 to transfer a force. Thus, the first pushing block 420 also moves downwards to be in close contact with the upper portion of the second pushing block 430. Here, the pushing bar 410 moves downwards along with the first pushing block 420 while the ratchet gear 411 is supported by the first pawl 421 of the first pushing block 420.

Thereafter, referring to FIG. 5C, when a user's pressing force is released, the first pushing block 420 is moved upwards by the second spring 460. In this case, the upward movement of the pushing bar 410 is limited while the ratchet gear 411 is supported by the second pawl 431 of the second pushing block 430, and only the first pushing block 420 is moved upwards. The first pawl 421 of the first pushing block 420 is moved upwards relative to the ratchet gear 411.

Meanwhile, the cap 300 becomes distant from the second pushing block 430 by the second spring 460, and the upward movement of the cap is limited by the cap support portion 110 so that the cap is moved to an initial position thereof as shown in FIG. 5A.

Consequently, due to one cycle of FIGS. 5A to 5C, the pushing bar 410 is spaced downwards by a predetermined distance, and the cap 300, the first pushing block 420, and the second pushing block 430 are restored to their initial positions.

Figure 6:
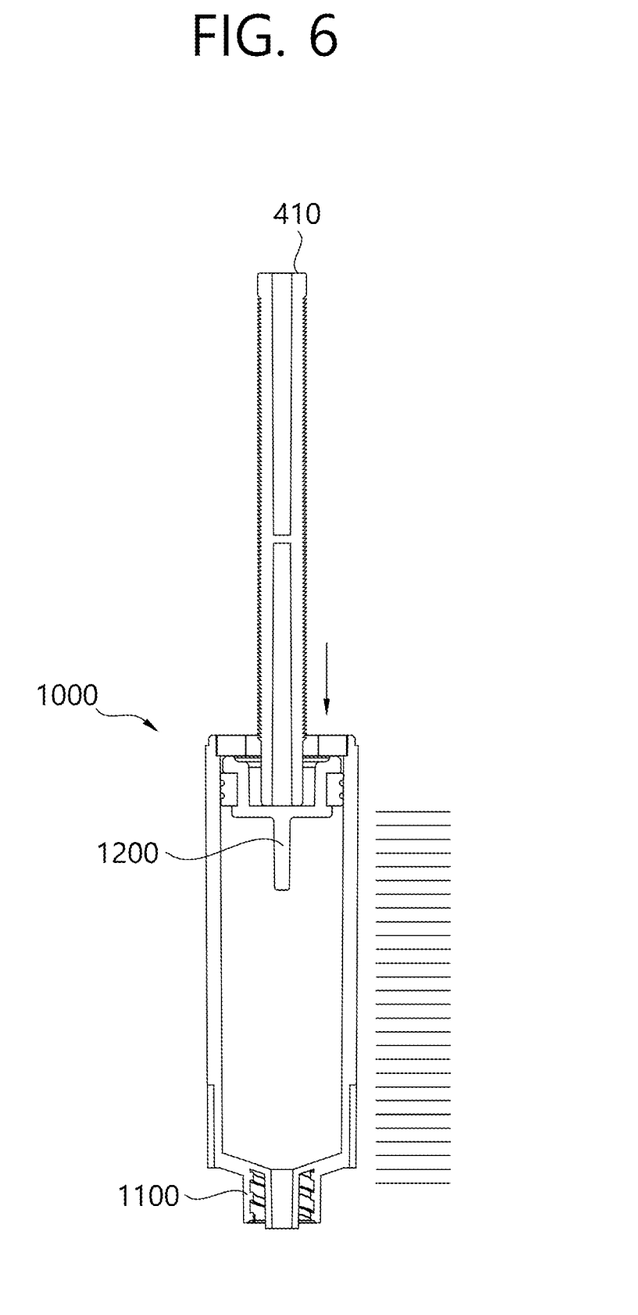
FIG. 6 is diagram showing the position of a piston which is moved by the repetitive operation of a fixed-quantity moving module.

FIG. 6 is diagram showing the position of the piston 1200 which is moved by the repetitive operation of the fixed-quantity moving module 400.

The pushing bar 410 is moved down to a predetermined distance by one pushing operation through the process of FIGS. 5A to 5C. Meanwhile, since the lower end of the pushing bar 410 supports the piston 1200 of the syringe 1000, a user may inject a fixed quantity of liquid medicine due to one pushing operation. Such an operation is repeatedly performed, so a fixed quantity of liquid medicine may be supplied for each pushing operation. The user may repetitively perform the pushing operation until the liquid medicine held in the syringe 1000 is used up. Meanwhile, the moving distance of the pushing bar 410 due to one clicking may be determined by the size of the tooth of the ratchet gear 411. In other words, when the vertical length of the tooth of the ratchet gear 411 is larger, one moving unit distance may be increased and thereby the injected liquid medicine may also be increased. Furthermore, the moving distance of the pushing bar which is moved by clicking the cap once may be determined by an initial set distance between the first pushing block 420 and the second pushing block 430. In other words, the quantity of the injected liquid medicine may be adjusted in response to a distance by which the first pushing block 420 is moved down by the clicking operation.

Hereinafter, a preparation process performed by a user to use the device for injecting the fixed quantity of liquid medicine according to the present disclosure will be described with reference to FIGS. 7 to 9.

Figure 7:
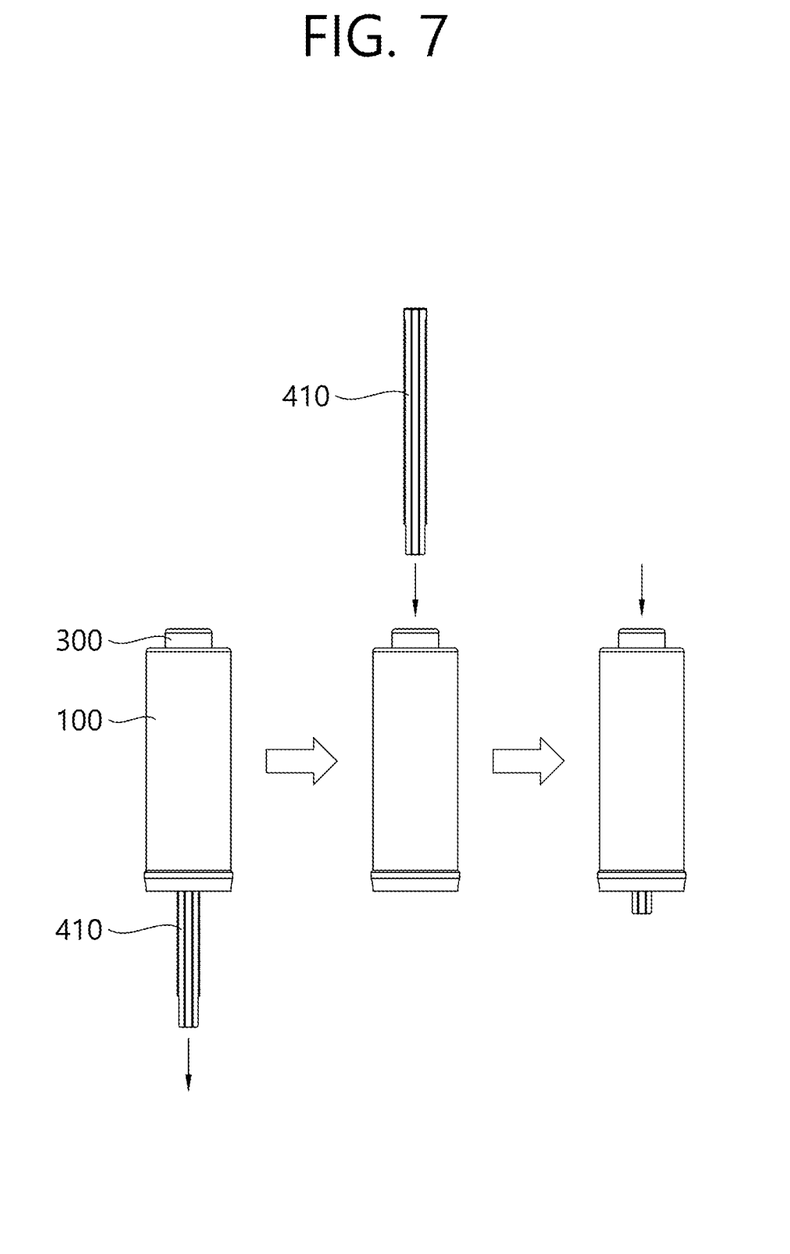
FIG. 7 is a diagram showing a concept of resetting the position of a pushing bar.

FIG. 7 is a diagram showing a concept of resetting the position of the pushing bar 410.

As described above, only the downward movement of the pushing bar 410 is permitted by the operation of the first pushing block 420 and the second pushing block 430. Therefore, when the ratchet gear 411 is removed from the first pawl 421 of the first pushing block by a user's repetitive pushing operation, the pushing bar is not moved any longer.

Therefore, the user disassembles the upper housing 100 and the lower housing from each other, and pulls the pushing bar 410 downwards from the upper housing 100. Subsequently, the user aligns the pushing bar with the hollow portion formed in the cap 300 while maintaining the direction of the pushing bar 410, and then pushes the pushing bar downwards. Here, the pushing bar is pushed downwards to a position where the ratchet gear 411 of the pushing bar 410 interacts with the first pawl 421 and the second pawl 431, thus completing the reset. Therefore, after the user resets the position of the pushing bar and replaces the syringe with another one, the device for injecting the fixed quantity of liquid medicine may be reused. Meanwhile, for the convenience of a user, the vertical length of the cap 300 may be determined such that the ratchet gear 411 of the pushing bar 410 engages with the second pawl 431 when the upper end of the pushing bar 410 is aligned with the upper end of the cap 300.

Figure 8:
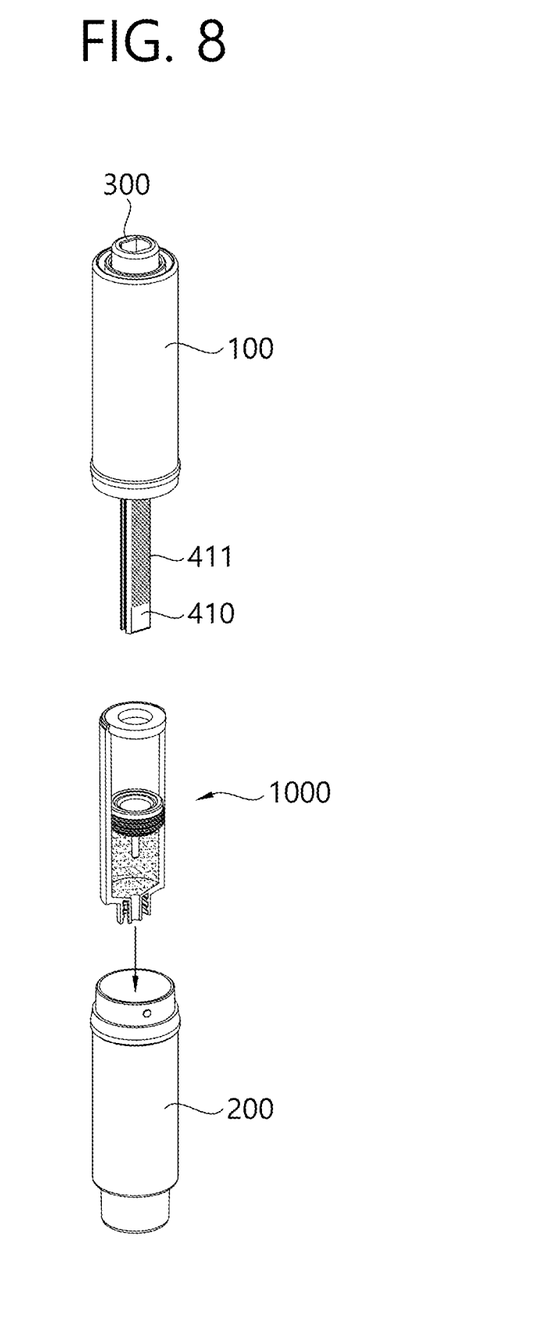
FIG. 8 is a diagram showing a concept of inserting a syringe into a lower housing.

FIG. 8 is a diagram showing a concept of inserting the syringe 1000 into the lower housing 200. Referring to FIG. 8, a user installs the syringe 1000 holding the liquid medicine in the second cavity 201. In this case, the downward removal of the syringe 1000 is prevented by the syringe support portion 210 provided on the lower portion of the lower housing 200.

Figure 9:
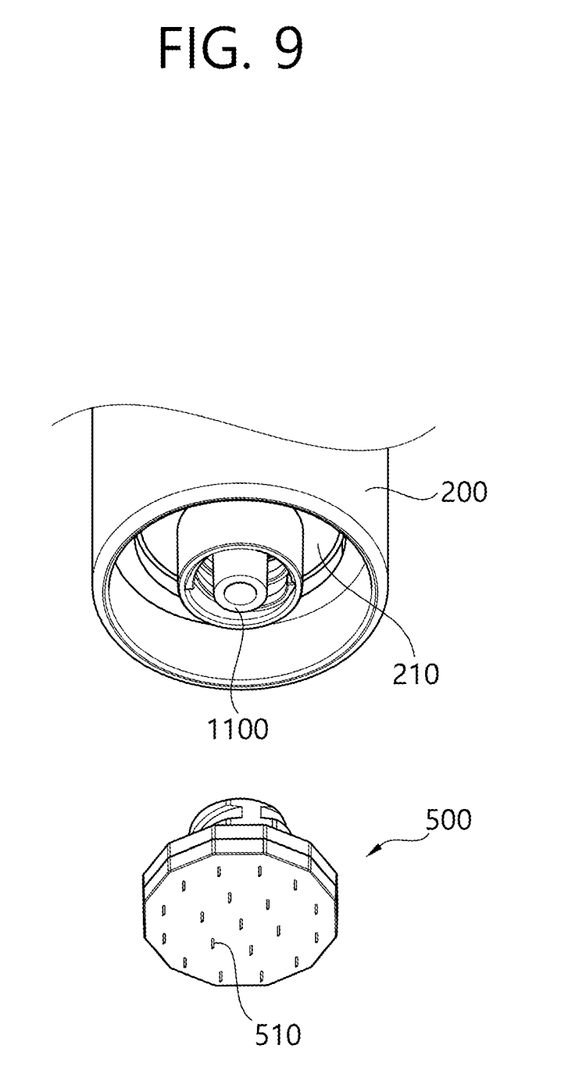
FIG. 9 is a conceptual diagram showing the fastening operation of a tip.

FIG. 9 is a conceptual diagram showing the fastening operation of the tip 500.

Referring to FIG. 9, after a user installs the syringe 1000 in the second cavity 201, the upper housing 100 is fastened to the lower housing 200 to finish a preparation for use. When the upper housing 100 and the lower housing 200 are fastened to each other, they should be aligned and fastened in a state where the lower end of the pushing bar 410 is inserted into the syringe 1000. Preferably, the pushing bar 410 is reset in position on the upper housing 100 and then is fastened.

Hereinafter, the use of the device 1 for injecting the fixed quantity of liquid medicine according to the present disclosure will be described with reference to FIGS. 10 and 11.

Figure 10:
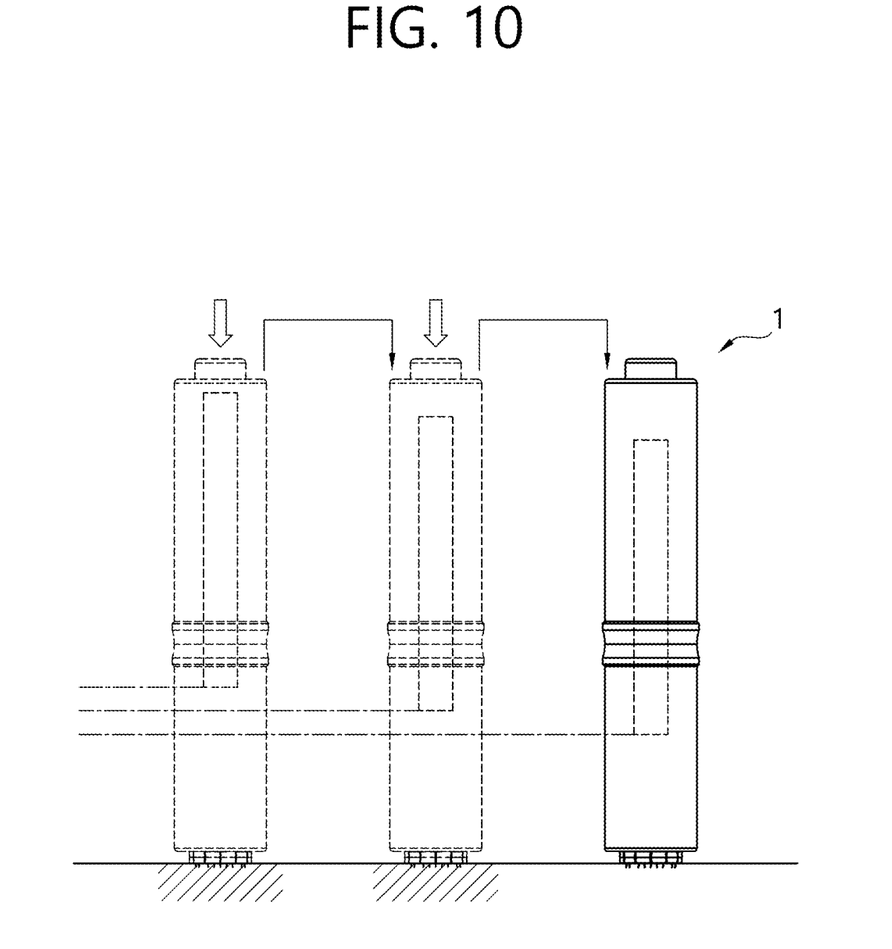
FIG. 10 is a diagram showing a use state of the device for injecting the fixed quantity of liquid medicine according to the embodiment of the present disclosure.

FIG. 10 is a diagram showing the use state of the device 1 for injecting the fixed quantity of liquid medicine according to the embodiment of the present disclosure.

Referring to FIG. 10, the device 1 for injecting the fixed quantity of liquid medicine according to the present disclosure may perform an injecting operation once by a user's pushing operation. Subsequently, after the user shifts the device 1 for injecting the fixed quantity of liquid medicine to a different position, the injecting operation may be performed once through the pushing operation. Thereafter, after the user shifts the device 1 for injecting the fixed quantity of liquid medicine to another position, the injecting operation may be performed once through the pushing operation. Consequently, the user may supply a fixed quantity of medicine to a treatment site of a large area using one syringe 1000. Although an example in which one pushing operation is performed at each injecting position is shown in the drawing, this is merely illustrative, and a user may adjust an injection quantity by performing multiple pushing operations at one position depending on a required injection quantity of the liquid medicine. Even in this case, a total quantity of delivered liquid medicine may be grasped by multiplying the quantity of the liquid medicine determined in one pushing operation and the number of pushing operations.

Figure 11:
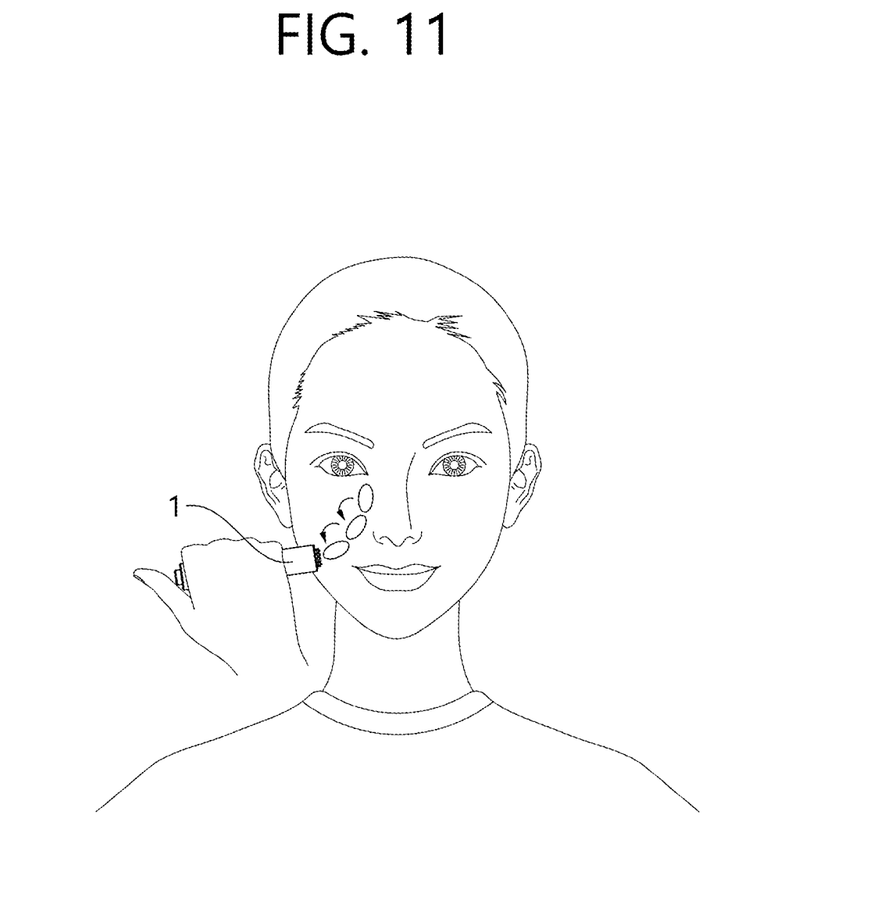
FIG. 11 is a diagram showing another use state of the device for injecting the fixed quantity of liquid medicine according to the embodiment of the present disclosure.

FIG. 11 is a diagram showing another use state of the device 1 for injecting the fixed quantity of liquid medicine according to the embodiment of the present disclosure.

As shown in the drawing, the device 1 for injecting the fixed quantity of liquid medicine according to the embodiment of the present disclosure may be formed in a pen type, and may be configured to be held and manipulated with one hand. A user may inject the liquid medicine by pressing the cap 300 with the thumb while holding the device 1 for injecting the fixed quantity of liquid medicine. Meanwhile, when it is required to evenly inject the liquid medicine into a large area such as the face, a user may displace the device 1 for injecting the fixed quantity of liquid medicine cap 300 while holding the device with one hand, may inject the liquid medicine by pressing the cap 300, and then may be shifted to another position. In this way, the same process may be repeated.

As described above, a device for injecting a fixed quantity of liquid medicine according to the present disclosure is advantageous in that a user can operate the device with one hand to inject a fixed quantity of medicine into various areas, thus maximizing operability and convenience.

Furthermore, the device is advantageous in that it is possible to maximize medicine delivery efficiency even when operated by a person who is not a medical staff not in a hospital but at home.

What is claimed is:

1. A device for injecting a fixed quantity of liquid medicine, the device comprising:
   an upper housing through which a first cavity is vertically formed;
   a lower housing configured to be connectable to a lower portion of the upper housing, with a second cavity being vertically formed through the lower housing;
   a cap disposed in an upper portion of the first cavity, and configured such that at least a portion thereof linearly reciprocates in the first cavity; and
   a fixed-quantity moving module moved downwards by a preset distance for each vertical reciprocating movement of the cap to push a piston of a syringe,
   wherein the fixed-quantity moving module comprises:
   a first pushing block configured to receive a force from a lower end of the cap and thereby move downwards;
   a second pushing block with a hollow portion provided in the first cavity under the first pushing block to be spaced apart therefrom by a predetermined distance; and
   a pushing bar extending to a predetermined length to be inserted into the upper housing,
   wherein the first pushing block and the second pushing block comprise a hollow portion formed vertically in which the pushing bar is inserted,
   wherein the pushing bar comprises at least one linear ratchet gear that is longitudinally formed on a side surface of the pushing bar,
   wherein the first pushing block comprises at least one first pawl, and the second pushing block comprises at least one second pawl,
   wherein the at least one first pawl and the at least one second pawl are configured to allow the pushing bar to move only in a downward direction, and
   wherein the piston moves by only linear movement of the pushing bar that is implemented by the first and second pawls engaging with the at least one linear ratchet gear.

2. The device of claim 1, wherein a lower portion of the pushing bar is configured such that at least a portion thereof is inserted into the syringe.

3. The device of claim 2, wherein a lower end of the pushing bar is inserted into the syringe to press the piston of the syringe.

4. The device of claim 2, wherein
   the at least one linear ratchet gear and the at least one first pawl are configured to move the pushing bar downwards and limit an upward movement thereof.

5. The device of claim 4, further comprising:
   a first spring provided between the cap and the first pushing block; and
   a second spring provided between the first pushing block and the second pushing block.

6. The device of claim 5, further comprising:
   a guide ring having a hollow portion formed in a vertical direction to allow the pushing bar to be inserted therein, and configured such that a first side thereof supports a bottom of the second pushing block and a second side thereof is fixed in the first cavity.

7. The device of claim 6, wherein the first pushing block is configured to move to a position where the first pushing block is in close contact with the second pushing block when the first pushing block is pressed downwards by the cap, and is configured to return to an original position thereof by the second spring when the first pushing block is not pressed.

8. The device of claim 7, wherein, when a downward force is transmitted to the first pushing block by the cap, the first pushing block moves downwards along with the pushing bar while limiting a relative movement of the at least one linear ratchet gear by the at least one first pawl, and the at least one second pawl of the second pushing block permits the relative movement of the at least one linear ratchet gear in a state where a position of the at least one second pawl is fixed.

9. The device of claim 8, wherein, when the downward force is removed from the first pushing block, the first pushing block is moved upwards by the second spring, the relative movement of the at least one linear ratchet gear is limited by the at least one second pawl of the second pushing block, and the at least one first pawl of the first pushing block permits the relative movement of the at least one linear ratchet gear.

10. The device of claim 4, wherein
a number of each of the at least one first and second pawls corresponds to a number of the at least one linear ratchet gear provided on the pushing bar.

11. The device of claim 10, further comprising:
a tip configured to be connected to a needle adapter of the syringe in a state where the syringe is inserted into the second cavity.

12. The device of claim 11, wherein the tip comprises a plurality of needles and an internal path configured to fluidly communicate with the needle adapter,
the plurality of needles each are configured to fluidly communicate with the internal path, and are arranged to be spaced apart from each other, a portion of a lower end of each of the plurality of needles protruding downwards from a lower surface of the tip.

* * * * *